United States Patent [19]
Weinbaum

[11] Patent Number: 5,914,596
[45] Date of Patent: Jun. 22, 1999

[54] COILED TUBING INSPECTION SYSTEM

[76] Inventor: Hillel Weinbaum, 7722 Moondance, Houston, Tex. 77071

[21] Appl. No.: 08/950,165

[22] Filed: Oct. 14, 1997

[51] Int. Cl.[6] .................................................. G01R 33/12
[52] U.S. Cl. .......................................................... 324/228
[58] Field of Search ..................... 73/597, 622; 324/228, 324/229, 237, 238, 240

[56] References Cited

U.S. PATENT DOCUMENTS

| | | | |
|---|---|---|---|
| 3,930,404 | 1/1976 | Ryden, Jr. ................................. | 73/622 |
| 3,955,425 | 5/1976 | Corneau ................................... | 73/622 |
| 4,027,527 | 6/1977 | Bennett et al. .......................... | 73/622 |
| 4,041,773 | 8/1977 | Hauldren et al. ........................ | 73/622 |
| 4,196,607 | 4/1980 | Youtsey et al. . | |
| 4,675,604 | 6/1987 | Moyer et al. . | |
| 4,725,963 | 2/1988 | Taylor et al. ............................. | 73/627 |
| 5,008,621 | 4/1991 | Jiles . | |
| 5,303,592 | 4/1994 | Livingston ........................... | 73/152.01 |
| 5,600,069 | 2/1997 | Girndt et al. . | |

Primary Examiner—Robert Raevis
Attorney, Agent, or Firm—Browning Bushman

[57] ABSTRACT

A non-destructive inspection system is disclosed for testing oilfield tubulars, and particularly for testing coiled tubing. The system includes a support housing and an inspection head removably positioned within the support housing and including a thru-bore for receiving coiled tubing. A magnetizing coil is provided for saturating the tubing while passing through the inspection head. The inspection head includes various sensors for detecting defects, including a plurality of flaw detector transducers circumferentially spaced about the thru-bore for outputting a signal indicative of a change in flux leakage, a plurality of wall thickness transducers for outputting a wall thickness signal indicative of a change in density of magnetic flux corresponding to tubular wall thickness, and at least two pairs of diameter transducers preferably lying along a first axis and a second axis perpendicular to the first axis for outputting signals indicative of the radial spacing between the transducers and adjacent outer wall of the tubular. The computer processes electrical signals from the inspection head and displays results to an operator in real time, and is interconnected via one or more electrical conductors with the inspection head.

20 Claims, 11 Drawing Sheets

COILED TUBING INSPECTION SYSTEM

FIELD OF THE INVENTION

The present invention relates to an inspection system for the non-destructive inspection of oilfield tubulars. More particularly, the present invention relates to an improved inspection system for the non-destructive testing of coiled tubing in a rapid and reliable manner. The system of the present invention is intended to simultaneously test for various types of defects in coiled tubing, including wall thickness defects, material flaws, longitudinal splits, and tubing diameter and ovality.

BACKGROUND OF THE INVENTION

Various types of systems have been devised for inspecting oilfield tubulars. U.S. Pat. No. 5,600,069 discloses an improved system for the ultrasonic testing for oilfield tubulars having various diameters. Oilfield tubular non-destructive testing equipment ideally satisfies several basic objectives. The system should be operator friendly and capable of being used by various inspection personnel. An inspection system also is preferably compact and may be both manufactured and maintained at a comparatively low cost. Most importantly, the system should be accurate in detecting various types of flaws, and should maintain that accuracy when oilfield tubulars are passing at a high rate through the system.

Non-destructive inspection systems primarily intended for testing coiled tubing present unique challenges. Those skilled in the oil patch appreciate that coiled tubing is distinguishable from conventional oilfield pipe, casing, and tubing in that coiled tubing is wound on a drum at the surface then passed downhole. Although lengths of coiled tubing may be joined by various types of connections, a length of coiled tubing is typically thousands of feet, rather than being 30 feet in length which is conventional for "rigid" oilfield tubulars with threaded connections. Since coiled tubing is inherently flexible, it has significant advantages over conventional threaded end oilfield tubulars, including relatively low cost and reduced time to pass the tubing downhole. This flexibility for coiled tubing presents unique inspection problems since the relatively thin wall of the coiled tubing must meet predetermined specifications, and since the tubing diameter and ovality must be within selected limits to minimize the likelihood of a coiled tubing ruptures. Coiled tubing may undesirably tend to elongate when an excessive axial force is applied to the coiled tubing, thereby reducing the wall thickness and the tubing diameter. Also, oilfield tubing tends to experience longitudinal splits at a rate significantly in excess of longitudinal splits in conventional oilfield tubing with threaded connector ends.

Several coiled tubing inspection systems have been devised, but none of these systems test for all of the defects commonly associated with coiled tubing, and most of these prior art systems are not highly accurate at detecting defects in coiled tubing. An inspection system manufactured by Rosen Inspection Technologies in Lingen, Germany tests for coiled tubing wall thickness and material flaws, but the system is bulky and expensive. Moreover, the Rosen inspection system does not test for tubing diameter and ovality, nor is the system well equipped to detect longitudinal splits in coiled tubing. A separate unit downstream from the Rosen flaw detection inspection system is required to measure the length of the tubing being inspected. Other prior art coiled tubing inspection systems, including a system manufactured by Stylwan Inspection in Houston, Tex., use a relatively small number of detectors, and are even less accurate at detecting most coiled tubing defects. Inspection systems that are specifically intended to test for coiled tubing diameter or ovality have been devised, but these systems do not test for various other types of defects in coiled tubing, including wall thickness, flaws, and longitudinal splits.

The disadvantages of the prior art are overcome by the present invention, and an improved coiled tubing inspection system is hereinafter disclosed. The inspection system is particularly designed for simultaneously testing for various types of defects in coiled tubing, and has a desired high accuracy at detecting those defects when coiled tubing is passed at a high rate through the inspection system.

SUMMARY OF THE INVENTION

The coiled tubing inspection system comprises a cylindrical housing with six centralizers and an electronics package housed in an aluminum case. Three centralizers circumferentially spaced at 120° are thus provided at the input to the housing and three similarly positioned centralizers are provided at the output to the housing. A plurality of transducers are housed on an inspection head positioned within the housing. A conductor cable connects the head to the electronic package in the aluminum case.

The cylindrical housing contains a magnetizing coil designed to bring to magnetic saturation the coiled tubing being passed through the housing. A diameter specific inspection head or cartridge, inserted within the housing, contains transducer arrays to detect total magnetic flux, magnetic flux leakage, and eddy current perturbations. The inspection head also houses four (4) eddy current (or piezoelectric) transducers that are positioned at 90° in order to measure the distance to the outer surface of the coiled tubing being inserted into the housing.

The aluminum case houses three computers: (1) a wall loss computer which calculates in tube quadratures the tubing wall thickness; (2) a diameter/ovality computer which determines the diameters of the tubing in two orthogonal planes and also determines a tubing off-center condition; and (3) a data acquisition streaming computer which displays a chart on a flat panel, with ports for a mouse, a printer and a keyboard. The case also houses flaw detecting amplifiers, differential eddy current longitudinal split electronics, a pulse width modulated constant current mag supply, a preset encoder/counter to monitor coil tubing length, and all electronic power supplies. The case is powered by a 120V AC source or optionally from other sources.

It is an object of the present invention to provide an improved non-destructive testing system particularly intended for testing oilfield coiled tubing. The system simultaneously detects for various types of defects commonly associated with coiled tubing, including material flaws, wall thickness variations, longitudinal splits, and diameter and ovality irregularities.

A related object of the invention is a coiled tubing inspection system which is highly reliable at detecting defects in coiled tubing, even when the coiled tubing is passed at a rate of from 30 feet per minute (9 meters per minute) to 180 feet per minute (55 meters per minute) through the system.

Yet another object of this invention is a coiled tubing inspection system which is relatively compact and may be manufactured and maintained at a relatively low cost.

A feature of the invention is that the various detectors do not contact the outer surface of the coiled tubing, thereby facilitating a high feed rate through the inspection system.

Another feature of the present invention is a coiled tubing inspection system which calculates a diameter of the coiled tubing along both an x-axis and a y-axis which are perpendicular, and then provides a calculation for determining the variation between the major axis and the minor axis of the coiled tubing in order to determine tubing ovality.

Still another feature of the present invention is that longitudinal splits in coiled tubing are detected with transducers which operate at a high frequency, thereby allowing for high sensitivity to this type of defect. Two detectors for testing longitudinal splits are axially spaced, and the difference in their outputs is indicative of an end of a longitudinal split in the coiled tubing.

It is a significant advantage of the present invention that the coiled tubing inspection system is relatively compact and may be easily moved to various coiled tubing inspection sites.

Another advantage of the coiled tubing inspection system is that the system is highly automated and may be reliably used by various non-destructive testing personnel.

These and further objects, features, and advantages of the present invention will become apparent from the following detailed description, wherein reference is made to the figures in the accompanying drawings.

DETAILED DESCRIPTION OF THE PREFERRED EMBODIMENT

Figure 3:
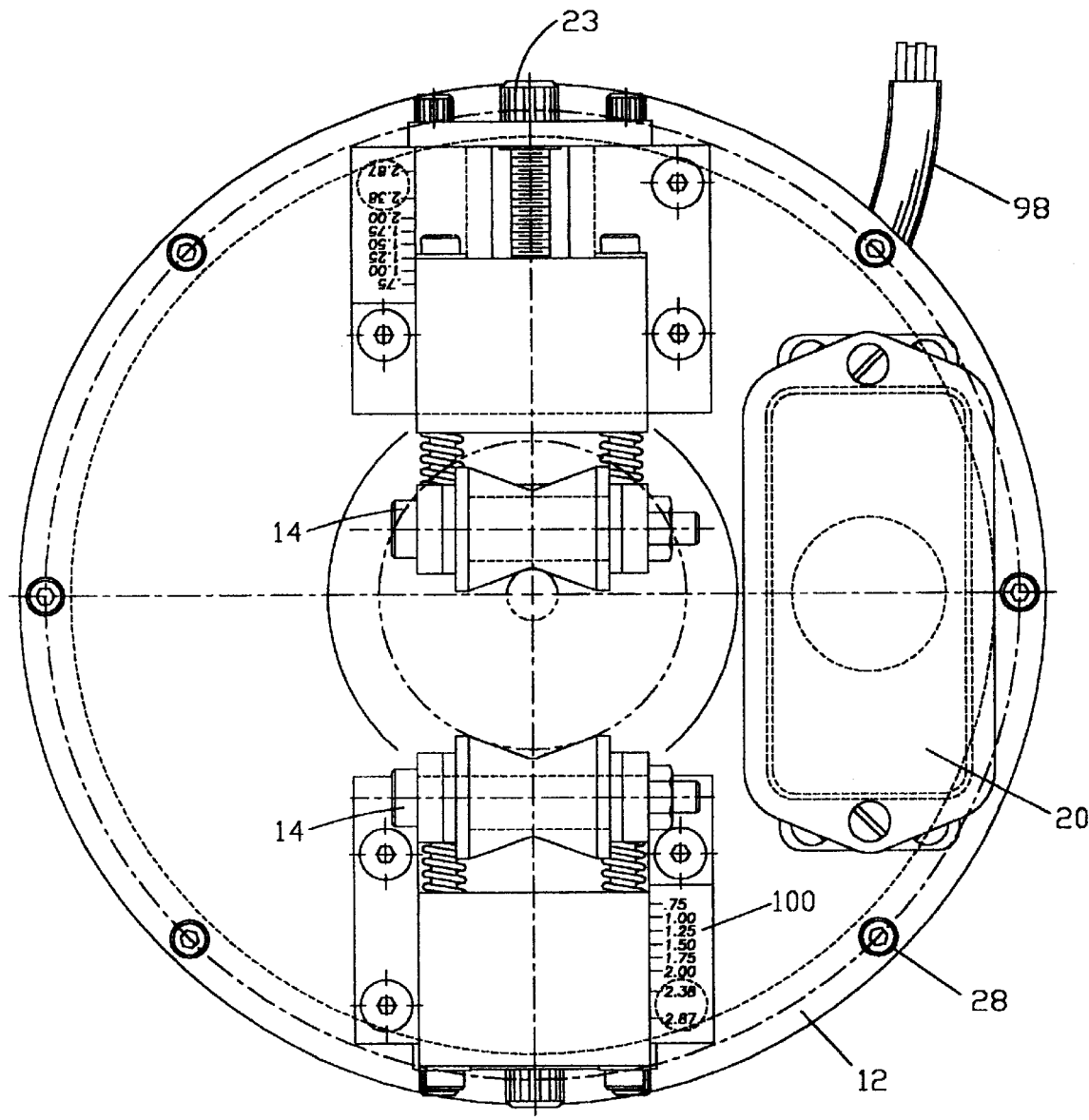
FIG. 3 is an end view of the inspection head and the mechanical centralizers shown in FIG. 1.
Figure 5:
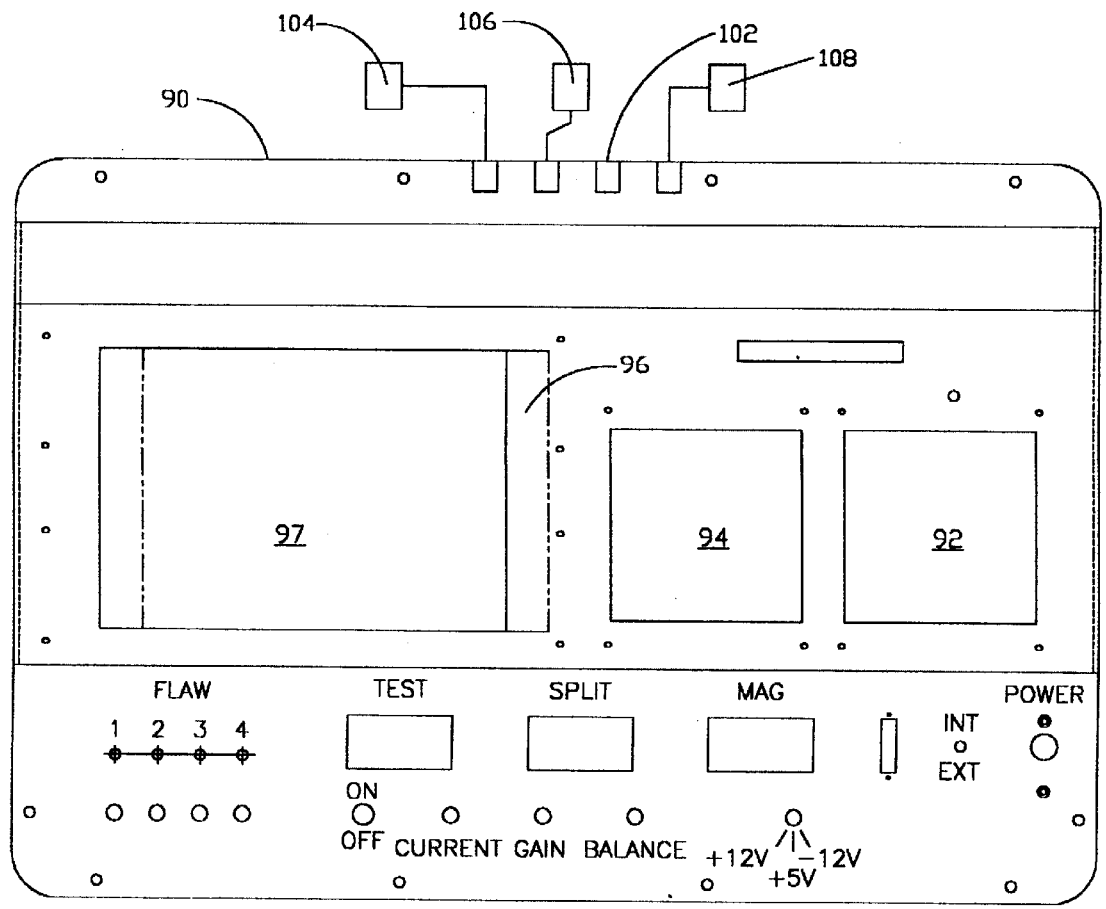
FIG. 5 is a pictorial view of the inspection case used with the inspection head.

The coiled tubing inspection system 10 comprises cylindrical housing 12 with roll centralizers 14 each at the input end 16 and the output end 18 of the cylinder, and an electronics package housed in an aluminum case 90 shown in FIG. 5. A plurality of transducers housed within an inspection head 30 are provided within the cylinder 12, as explained subsequently. End plates 24 and 26 secure the inspection head 30 therein with conventional screws 28, as shown in FIG. 3. A conductor cable 98 as shown in FIG. 3 leads to junction box 20 to connect the cylinder to the case 90 shown in FIG. 5. The cable both supplies power to the inspection head 30 and transmits signals from the head to the case 90. Alternatively, one cable may be used to supply power to the inspection head 30, and one or more other cables may connect the transducers in the head 30 to the electronic package in the case 90. Less desirably, wireless FM technology could be used to transmit transducer signals to the case 90.

Figure 1:
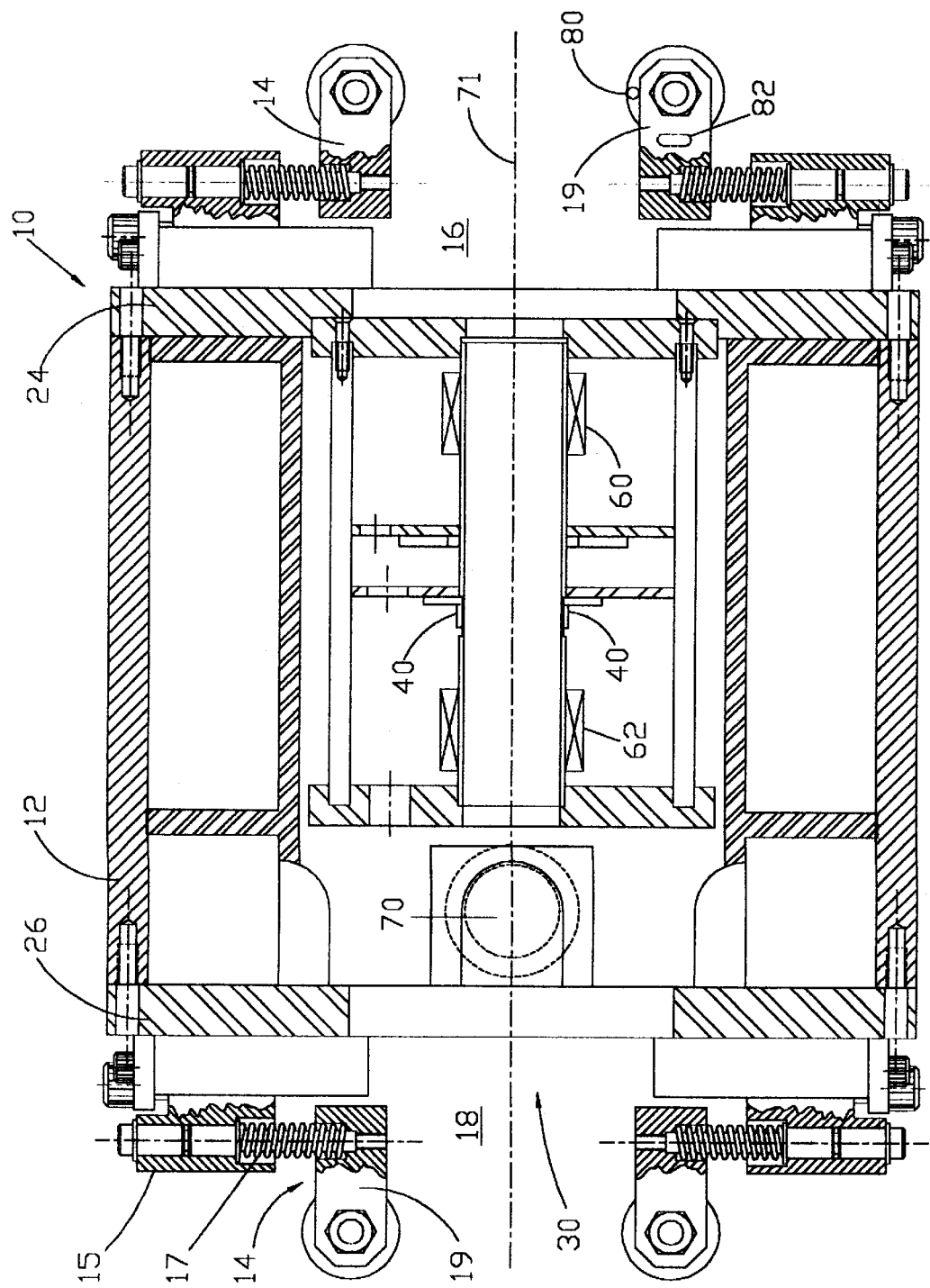
FIG. 1 is a cross-sectional view of a coiled tubing inspection cylinder and mechanical centralizers according to the present invention for centralizing coiled tubing passing through the housing during an inspection operation.
Figure 4:
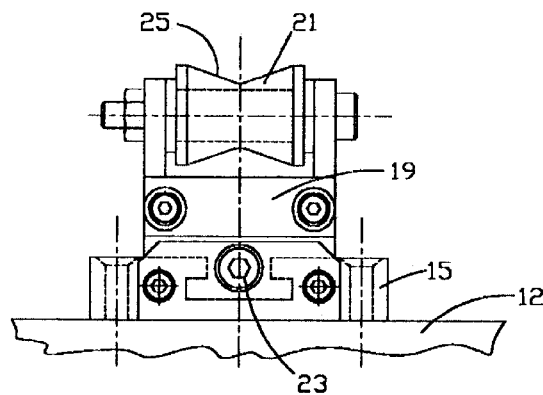
FIG. 4 is a detailed view of one of the centralizers shown in FIGS. 1 and 3.

Each of the centralizers 14 is mounted on a centralizer base 15, as shown in FIGS. 1 and 4. A coil spring 17 biases roller block 19 toward the coiled tubing, and is shown in FIG. 1 in its maximum diameter configuration for cooperating with an inspection head corresponding to the largest diameter coiled tubing to be inspected. Roller 21 is rotatably mounted on the block 19 for engaging the coiled tubing. Each roller 21 includes a v-shaped guide surface for rotating engagement with the coiled tubing while guiding the coiled tubing within the inspection head 30. A lead screw 23 provides for axial adjustment of the roller 21 relative to the housing 12. FIG. 3 illustrates the upper centralizer 14 in its radially innermost position for guiding a small diameter tubing, and the lower centralizer 14 in its radially outermost position for guiding a large diameter tubing. Markings on the base 15 provide a visual scale 100 for observing the position of the roller to guide a specific diameter tubing. Alternatively, specifically sized and non-adjustable rollers may be used, with the rollers sized for and replaced with the specific diameter inspection head.

Figure 2:
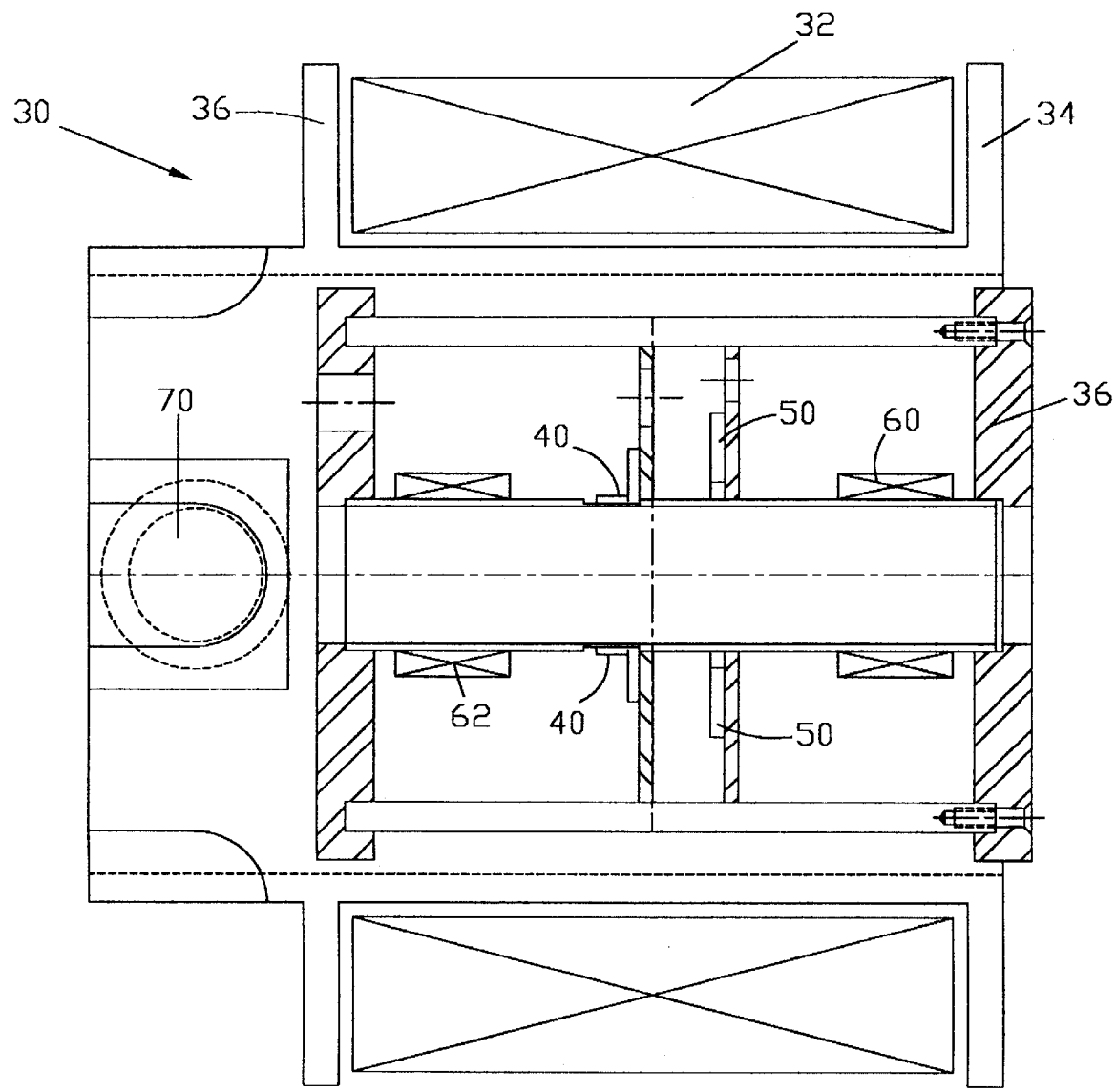
FIG. 2 is a detailed view, partially in cross-section, of the cylinder housing and the replaceable inspection head cartridge generally shown in FIG. 1.

The cylinder 12 houses the inspection head 30 shown in FIG. 2, which in turn houses a magnetizing coil 32 between flanges 34 and 36. The magnetizing coil 32 is designed to bring to magnetic saturation the coiled tubing being passed through the housing 12. A diameter specific cartridge 36, mounted within the inspection head 30, contains transducer arrays to detect magnetic flux leakage (flaw detection), changes in total magnetic flux (wall loss detection), and eddy current perturbations (longitudinal split detection). The head 30 also houses four (4) eddy current transducers that are positioned at 90° in order to measure the distance from each transducer to the coiled tubing being inserted into the cylinder, and thus serve as diameter and ovality detectors.

Transverse and Three Dimensional Flaw Detectors

Four arrays of Hall Effect transducers 40 are positioned around the coiled tubing to be inspected, and are mounted within the diameter specific cartridge 36. A different cartridge 36 is thus used for each different nominal diameter tubular to be tested. The transducers are positioned to detect flux leakage and are spaced from about 0.15 inches to 0.25 inches from the external surface of the incoming coiled tubing. For the smallest diameter coiled tubing to be inspected (¾" nominal diameter tubing), each array comprises six transducers for inspecting a 90° circumference of the tubing. For inspecting 2" nominal diameter tubing, each of the four arrays for inspecting a 90° circumference of the tubing comprises fifteen transducers. A cartridge for the largest diameter coiled tubing would include more transducers in each array. Each transducer array thus preferably includes a plurality of transducers circumferentially arranged to cover approximately 90° of the coiled tubing. At least twenty-four transducers are thus circumferentially spaced about the central bore in the cartridge 36 which is sized to receive a specific diameter coiled tubing. Each 90° array of flaw detectors thus detects transverse and three dimensional flaws in the material of the respective quadrant of coiled tubing adjacent that array.

Figure 7:
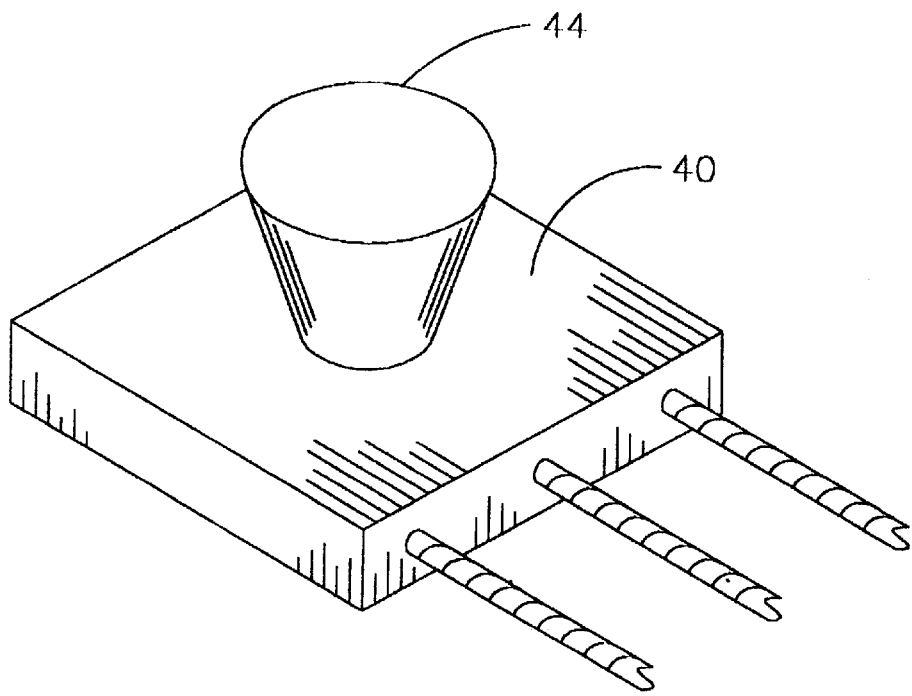
FIG. 7 illustrates a flow detector transducer with a conical flux concentrator above a transducer.

Allegro 3507 linear Hall Effect transducer was selected due to the higher sensitivity, scanning speed tolerance, high temperature stability, built in amplifier and voltage regulator. This transducer exhibits a typical 2.5 mv/Gauss sensitivity, although even higher sensitivity in excess of 4.0 mv/Gauss has been achieved. Each transducer is also aided by a conical flux concentrator 44 as shown in FIG. 7 that enhances detection and permits the liftoff (radial spacing) between the transducer and the tubing. The concentrator is fabricated from a magnetizing material, such as soft iron, and effectively makes the entire area of the transducer package (0.180 inches ×0.180 inches) a sensitive detector, rather than merely the 0.025 inches ×0.025 inches active element area of each transducer. The concentration 44 is thus spaced radially outward of each plate-like transducer 40. Concentrator 44 is optional, and transducers 40 each without a concentrator may be used for various applications.

Flux leakage around the Hall Effect transducer causes a change in the transducer voltage. Each array group is formed with matched transducers, with each transducer in the group wired in such a way that only the largest flux leakage indication for the array group dominates at any specific time, although that largest flux leakage signal from each array may be represented as either a positive signal or a negative signal. The magnetizing coil is polarized so that the flux leakage from the flaws generate a negative going voltage. The largest negative going voltage from the array dominates at a specific time. Sensed flux leakage from transducers in an array which do not sense the largest leakage value may thus be discarded by the computer.

The output from the detectors 40 are coupled via an additional 10 dB preamplifier to adjustable gain amplifiers located at the case 90. The preamplifier reduces the susceptibility to possible noise interference. The four amplifiers are combined to generate the largest positive indication and the largest negative indication at any instance. All signals are set to produce a positive going indication from the largest signal on the first trace, and a negative going indication from the second largest signal on the second trace. In other words, a positive flux leakage signal from one array may be combined with a negative flux leakage from a radially opposing array to provide a more accurate indication of a flaw. Furthermore, a linear reject circuit allows removal of small noise indications without affecting any signal exceeding the linear reject threshold. Individual switches permit enabling/disabling of any of the four (4) circuits.

As shown in FIG. 2, the plate-like transducers 40 are positioned at substantially a right angle to the plate-like transducer 50 discussed subsequently.

Wall Loss Detection and Alarms

The total magnetic flux allows non-contact determination of ferromagnetic materials type and their mass within a dual winding arrangement based on the Rowland Ring experiment performed over 120 years ago. Four arrays of Hall Effect transducers 50 each constituting ¼ of the circumference are positioned circumferentially around the tubing to be inspected. Each transducer 50 is turned 90° relative to the transducers 40. By positioning the flaw detector transducers and wall loss transducers at 90° from each other, a detector for sensing both radial and axial fields from the inspected tubing is obtained. A combination of wall and flaw information facilitates acceptance/rejection determination. If a flaw is located in a thick segment, it may be accepted. If a flaw is located in a thin segment, it may render it rejected. The computer may thus receive signals from both the flaw detector transducers and the wall thickness transducers and compare those signals to determine if a sensed flaw should result in a rejection signal.

The number of transducers 50 within each array will depend on the size of the coiled tubing being inspected, although six or more transducers 50 are preferably provided in each array. The four arrays can collect the total magnetic flux information. Wall thickness detection is thus not obtained in a conventional manner by detecting flux leakage, but rather is measured by detecting the reduction in the total magnetic flux density caused by the tubing, which is proportional to the wall thickness of the tubing. The thicker the tubing, the greater the reduction in magnetic flux density sensed by the transducers 50, which are spaced radially between the tubing and the magnetizing coil 32. When the transducers 50 are coupled to a computer, numerical values can be calculated to ascertain the thickness of the tube adjacent each array if other magnetic characteristics are held constant.

The computer is programmed to read the value of each quadrature array, filter out unqualified values and display the expected thickness of the tube in each quadrant based on the sum of the presumed valid signals from the transducers in each array. The computer also calculates deviation from expected nominal thickness valve. An analog voltage that is proportional to the difference between the largest wall reading and the nominal is output as "+WALL", and an analog voltage that is proportional to the difference between the nominal and the smallest wall reading is output as "−WALL".

The computer is equipped with an alarm circuit if a wall reduction in any portion of the tubing corresponding to an array exceeds a predetermined amount. The small 8 bit computer (Z 180) goes through a complete reading and calculating cycle in ⅟₃₅th of a second. A "calculation" includes gathering four (4) wall indications, processing (filter and BOXCAR) and scaling, comparing to an alarm level and, when appropriate, triggering alarms. There are two modes of operation: (1) If the display is to be updated, the computer performs at a rate of 14 "calculations" per second; (2) If the display is not to be updated, the computer performs at a rate of 35 "calculations" per second. This computer features battery backup to calibration values and a complete linearization routine (Y=mX+C) for each read input. (Y is output, X is the input, m is the linearization slope, and C is offset value). Mathematical calculations and integration formulas are standard and may be obtained from prior art. Other features include a BOXCAR averaging system for incoming data points, and print-out capability. The BOXCAR system averages each measured data point with the prior three data points from that transducer to produce a more reliable measurement.

A wall thickness detection concept was employed in the InSpect 1001 inspection system manufactured by IST, Inc. in Houston, Tex., which is a prior art system used for non-destructive testing of drill pipe. The prior art system detected wall thickness as a function of the output from each transducer. The present system adds or sums the presumed valid wall signals from the transducers from each of the four quadrants, and ensures that the sum from each array is within maximum and minimum limits corresponding to the particular coiled tubing size being tested. This summing of the signals from the sensors in each array is an effective technique for evaluating very small wall loss variations and "telescope tubing" variations associated with coiled tubing.

Detection of Longitudinal Splits—Eddy Current

A pair of coils 60, 62 positioned axially about six inches apart are wired in a differential manner. The coils are energized with an oscillator within a card in the case 90 and coupled to a potentiometer balanced circuit. Once balanced within the magnetic saturating circuit, the output of each coil is continuously compared to the output from other coil, and amplified to denote and emphasize the difference.

As each coil impedance is subject to the tubing material within it, the difference between the impedance of the coils is "zero" if both generate and observe an equal amount of eddy currents (i.e., absolute value of impedance (A) from coil 60–absolute value of impedance (B) for coil 62=0). If one coil generates and observes more (or less) eddy current disturbance due to a longitudinal split in the tubing, while the other axially spaced coil is not responsive to the split at the same time (since the split is not radially adjacent that coil), the difference will cause a significant impedance difference. This indication is proportional to the depth and length of the split. By controlling the frequency of the oscillator while the tube is in the magnetic field, the depth of penetration of the split can be determined. A high frequency oscillation will penetrate less than a low frequency oscillation, and will exhibit higher sensitivity to external surface longitudinal flaws. The frequency of the eddy current can be adjusted. For some implementations, more than one frequency can be generated. If only external splits are to be detected, a frequency of from 1 kHz to 5 kHz is selected. If only internal splits are to be detected, a frequency of 500 Hz may be selected. If both external and internal splits are to be located, a mixture of two or more frequencies will allow further identification of the splits and determine if a split is on the external surface (high frequency, no lower frequencies), internal surface (low frequency, no higher frequencies), or both surfaces (both high and low frequencies).

A unique feature of the circuit is the ability of the detection system to balance with one rather than two potentiometers. The circuit produces two outputs: (1) an AC output to the computer that will report a comparison between the coils at frequency intervals, and (2) a DC output to the digital meter that will report a comparison between the coils that last 10 cycles or more. A digital meter monitors the DC output and facilitates balancing of the arrangement.

Each coil 60, 62 is a 1000 turns detector wound to a length of 0.75 inches, with a AWG 28 wire. The circuit board used is an IST 3122. The use of two axially spaced coils and the detection of a split in the coiled tubing based on the difference in output between the coils is thus an important feature of this invention. Moreover, this comparison and split coil detection is made in real time, and may be visually displayed to the inspection system operator.

The Diameter/Ovality Detector

Four eddy current transducers 70 as shown in FIGS. 1 and 2 are placed 90° apart at a fixed distance from a centerline 71 of the bore through the inspection head 30. A coiled tubing having a diameter smaller than the distance between opposing transducers (placed 180° apart) is inserted into the inspection head 30. Each transducer reports the distance from its surface to the outer diameter surface of the tube. By adding the combined distance between opposing transducers and the adjacent outer wall of the tubing and subtracting that sum from the distance between the opposing transducers, a tube diameter axis is calculated. The process is duplicated for the other two transducers to determine the second diameter (y-axis diameter) at 90° relative to the first diameter (x-axis diameter). In a preferred embodiment, the x-axis diameter and y-axis diameter are perpendicular. If more than two diameters are provided, they may be equally spaced about the tubing, i.e., four diameter may be measured at 45° spacings. In each case, one diameter is substantially inclined relative to another diameter to detect ovality.

Figure 6:
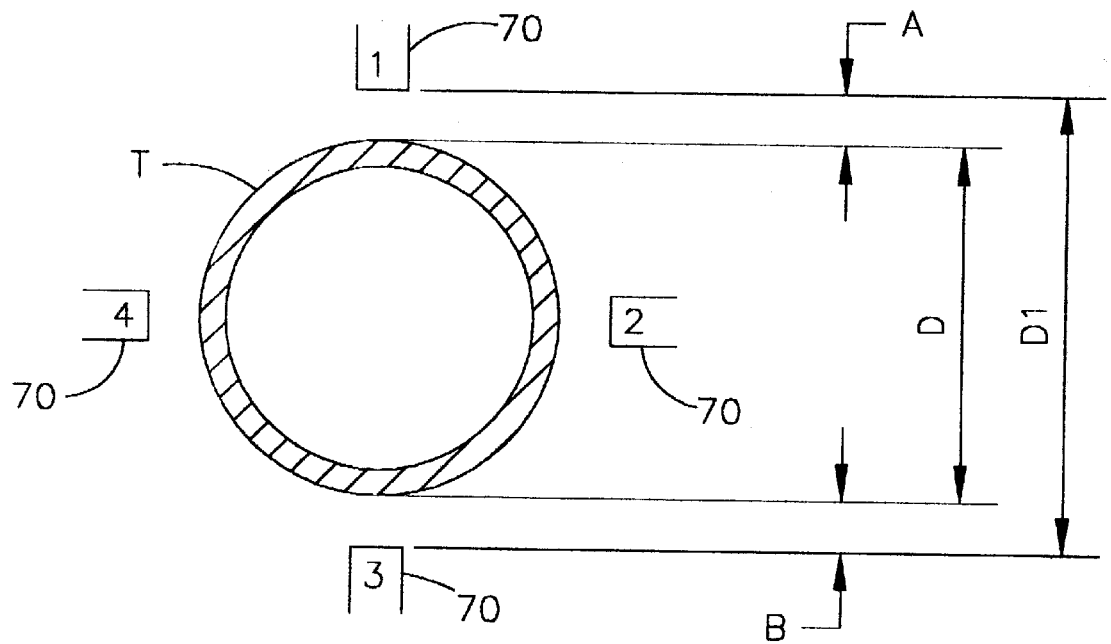
FIG. 6 is an end view of a diameter/ovality sensor arrangement according to the present invention.

Referring to FIG. 6, the diameter D of the coiled tubing is thus the diameter D1 of the spacing between radially opposing detectors 70, less the combined spacings A and B between opposing transducers and the outer wall of the tubing. Accordingly, D=D1−(A+B). Suitable eddy current transducers are manufactured by Truck and Gordon. Alternatively, ultrasonic or piezoelectric transducers manufactured by Massa Products Corporation in Hingham, Mass., may be used. The electronics for ultrasonic transducers is complicated and ultrasonic transducers are temperature sensitive, although their overall sensing capability is greater than eddy current sensors. Ultrasonic transducers may thus easily replace the eddy current transducer disclosed herein for detecting ovality and diameter of the tubing.

In order to calibrate the system, the distance between opposing transducers and the actual tubing diameter should be known. The operator "ENTERS" Distance and Diameter and the computer linearizes the reading of opposing transducers. The individual readings are also displayed for convenience. The radial distance between each transducer 70 and the outer wall of the coiled tubing is then sensed. The computer also calculates if the tubing is not in the exact center of the inspection head 30 and reports off-center conditions. An alarm is triggered when either the sensed tubing x-axis diameter or the sensed y-axis diameter is not within selected limits. When both under diameter and over diameter conditions are present but each are within selected limits, the determined effective diameter of the tubing may be satisfactory. Tube necking and tube ballooning are reported as "−DIAM" and "+DIAM", respectively.

The computer also produces two analog outputs with indications proportional to the deviation of diameter. Ovality can be detected by observing that one tube axis is larger than the other tube axis. The computer thus calculates the differences between the larger diameter (major axis of the oval) and the smaller diameter (minor axis of the oval) to determine if ovality is within preselected limits.

Tubing Length Monitoring

Referring again to FIG. 1, a magnet 80 is embedded in at least one of the centering rollers 21 with the South pole toward the outside. With every wheel revolution, the magnet passes in front of a bipolar Hall effect switch 82 (Allegro 3177) placed on the supporting arm 19. When the Hall Effect element is subjected to about 100 Gauss, the output is grounded. A preset counter relates the number of turns of the wheel to a fixed length of the passing tube. The preset counter is set for each diameter of tubing to be inspected. The output is used to determine longitudinal position, i.e., both the length of coiled tubing passing through the test equipment and the axial position along the coiled tubing when a particular defect is detected.

Alternate applications call for embedding two magnets, one with the South Pole exposed and one with the North Pole exposed. The magnets are located 180 degrees apart. Each magnet triggers two (2) Hall devices placed in a yoke arm. The order of the triggering determines the direction of the wheel (H1 before H2, or H2 before H1), and the opposing orientation magnets allow alternating the on/off positions of the Bi-direction Hall. If the Hall elements are placed in a ferromagnetic wheel, the magnetizing forces used to magnetize the coiled tubing may diminish the effectiveness of the magnets. The wheel should be of a nonmagnetic stainless and protected from the external magnetic field. An alternative implementation may call for placing an optical encoder on the shaft of the wheel.

Inspection Case

The aluminum case 90 as shown FIG. 5 houses three components: (1) a wall loss computer 92 which calculates in tube quadratures the remaining wall thickness; (2) a diameter/ovality computer 94 which determines the tubing diameters in two orthogonal planes and also determines a tubing off-center condition; and (3) a data acquisition streaming computer 96 which displays a chart on a flat panel 97 to the operator. Ports 102 for a connected mouse 104, printer 106 and keyboard 108 may also be provided. The case 90 also houses a four channel transverse and three dimensional flaw detecting circuitry, a differential eddy current longitudinal split electronics, a pulse width modulated constant current mag supply, a preset encoder/counter to monitor coil tubing length, and all electronic power supplies. The case 90 is powered by a 120V AC source or optionally from other sources. A suitable data acquiring computer is a DI 200 with 486 DX2.

Test results are preferably approximately 20 times per second. If the tubing is moving at 1 ft./second through the test unit, a test is made for approximately one-half inch of coiled tubing. If the tubing is moving at 2 ft/second, a complete test is performed every one (1) inch of coiled tubing.

A computer program and an interface card permit the generation of a paper trace-like display on a high brightness TFT flat panel display. Operating under Windows 95, a continuous chart-looking display simulates an eight channel ink chart recorder.

The screen 97 allows for fast data acquisition, streaming recording to Hard Drive. Recorded files can be stored on a floppy disk or a Zip disk. A marker can be inserted at selected locations with an automatic time/date stamp. The screen is programmed to produce a white background with blue grid lines and red traces, but a pallet of other colors is available.

System Electronics

Suitable system electronics are depicted in FIGS. 8–13. The wall thickness, flaw, and split detector transducers may be packaged as a subassembly separate from the diameter/ovality transducers 70. The magnetizing coil and the preamp or junction box 20 are also shown as part of the inspection head 30. The electronics case 90 may house a system computer and specific defect electronics. A test circuit, a supply for the magnetizing coil, and power supplies are also housed in the case 90.

Figure 8:
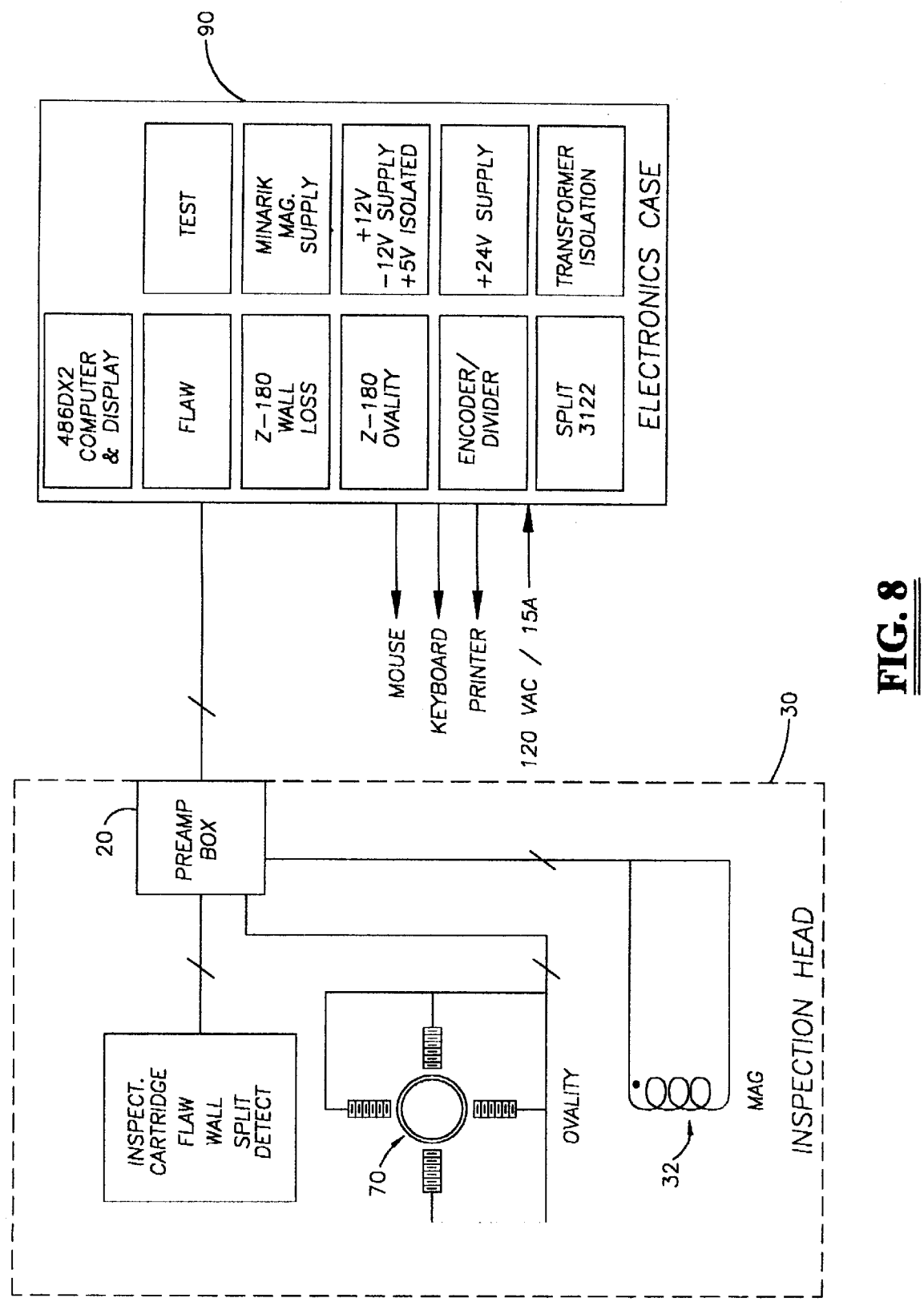
FIG. 8 is a block diagram of the typical system components for the inspection head and electronic case for the system according to the present invention.
Figure 9:
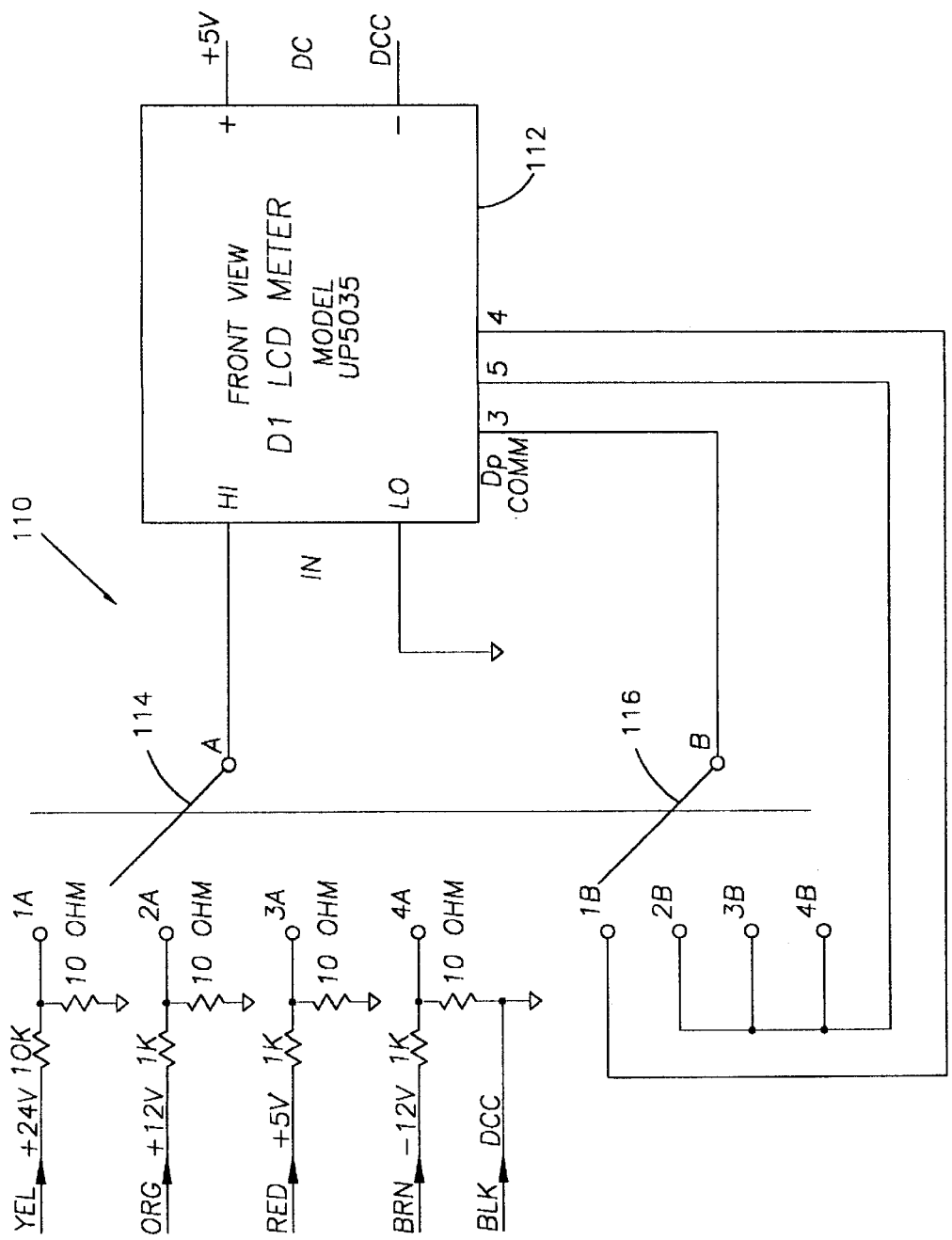
FIG. 9 is a test circuit for the system according to this invention.

FIG. 9 discloses a suitable test circuit 110 generally shown in FIG. 8. This circuit may be used to route a selected power supply voltage to the test meter 112. Switches 114 and 116 allow the operator to choose a +24 volt, +12 volt, +5 volt, or −12 volt to be displayed on the meter 112 so that the system electronics may be thoroughly checked at the desired voltage settings.

Figure 10:
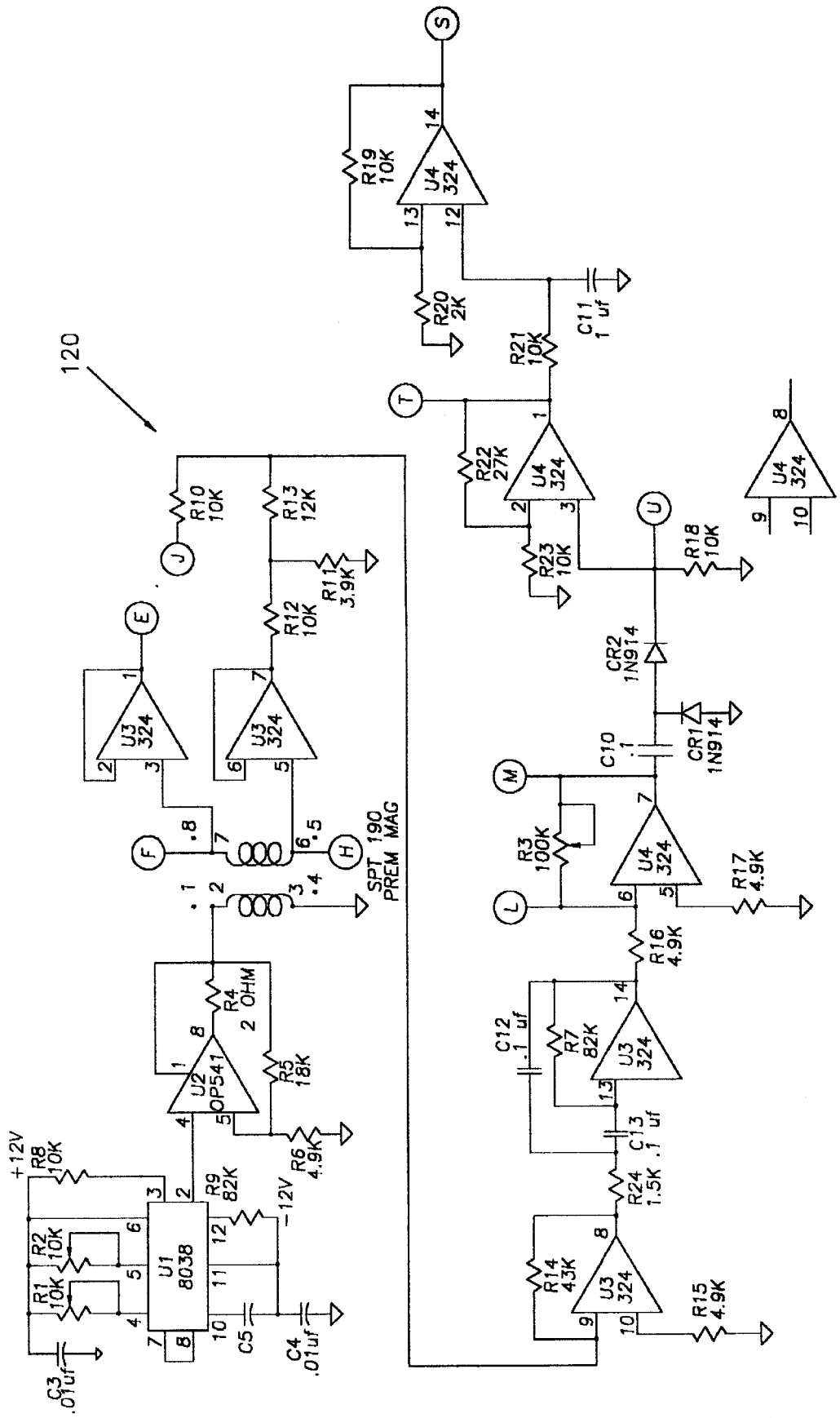
FIG. 10 is a suitable detector circuit for sensing a split in the coiled tubing.

FIG. 10 shows an IST 3122 split detector circuit 120 for receiving eddy current signals from the coils 60, 62. A 1 kHz, 6 volt AC signal may be generated and sent to the pair of coils 60, 62, which may be spaced axially 6 inches apart. When a longitudinal split defect is present under one coil but not the other coil, the circuit 120 detects the difference in the load on that coil compared to the other coil due to the inductive reactance of the coil. This difference may be output as a voltage signal to a digital meter 122 shown in FIG. 13 and also to the computer interface card within the case 90.

Figure 11:
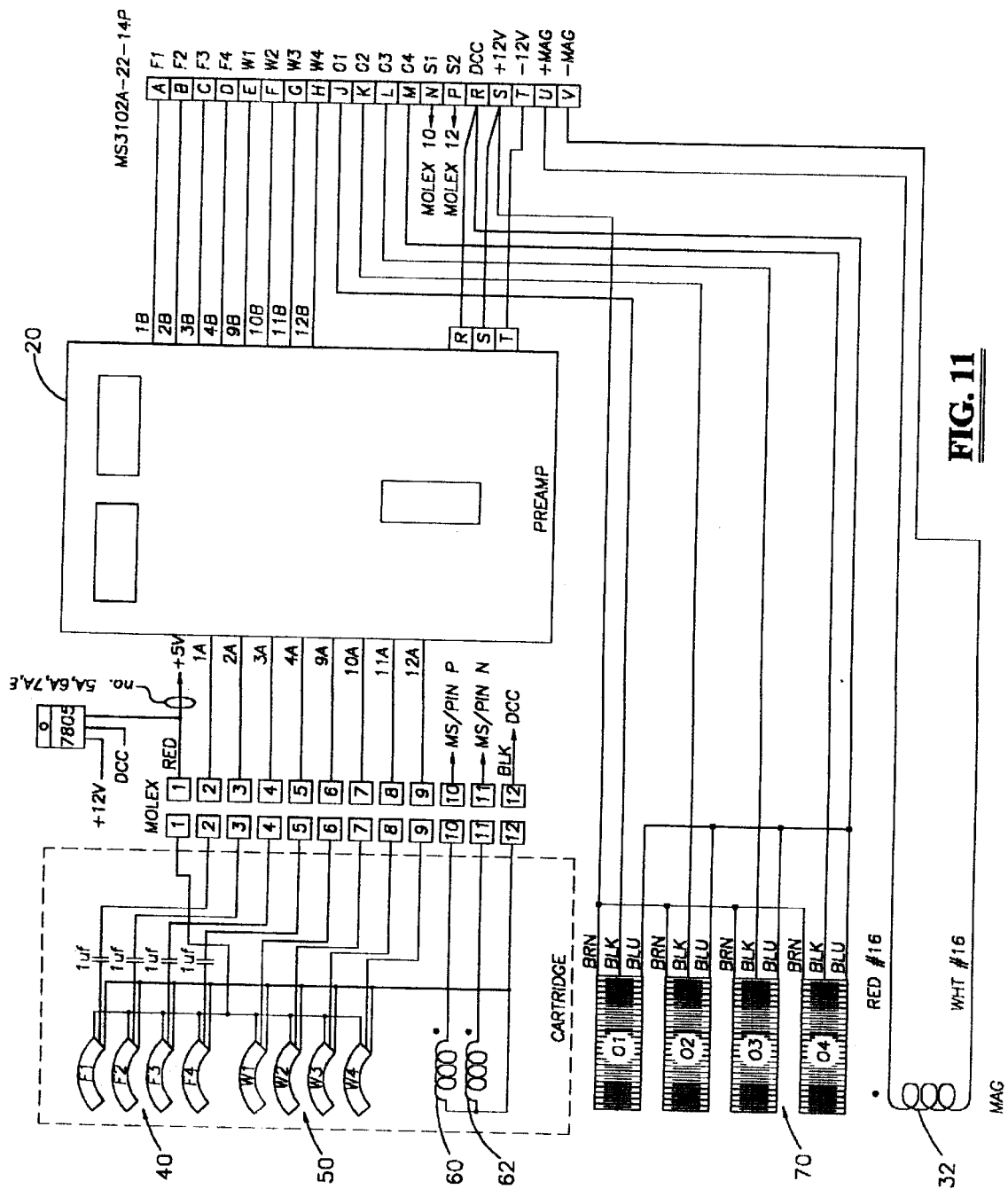
FIG. 11 is a junction circuit illustrating the preamp box, and the cartridge housing the flaw, wall thickness and split tubing detectors. The diameter and ovality detectors and the magnetizing coil which functionally need not pass but conveniently do pass through the junction box are also shown in FIG. 11.

FIG. 11 illustrates suitable wiring to and from the preamp box 20. The preamp box 20 serves as a junction for the wiring from the inspection head. As previously noted, the diameter and ovality sensors 70 and the conductors to the magnetizing coil 32 may actually pass through the junction box and then to the case 90. Signals from the split detector coils 60, 62, the diameter and ovality sensors 70, and power to a magnetizing coil 32 functionally may pass uninterrupted, however, through the preamp box 20. The output from the flaw sensors 40 and wall thickness sensors 50 is routed through a preamplifier to boost output levels and reduce noise, and then to the output connector. The diameter and ovality sensors effectively act as proximity switches that produce changes in output voltage when the distance between the sensors is interrupted by the presence of the tubing. As previously noted, magnetic coil 32 is used to produce a magnetic flux field in the tubing being inspected.

Figure 12:
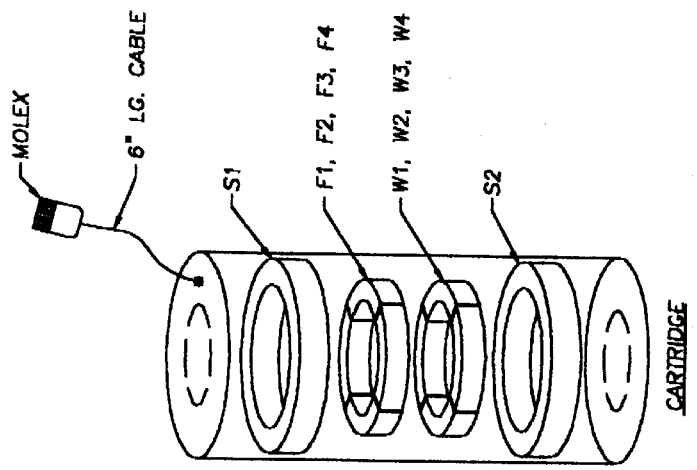
FIG. 12 is an elongated view of the circuit for detecting flaws, wall thickness, and tubing splits as generally shown in FIG. 11. A cartridge housing each of the detectors is also pictorially illustrated.
Figure 12:
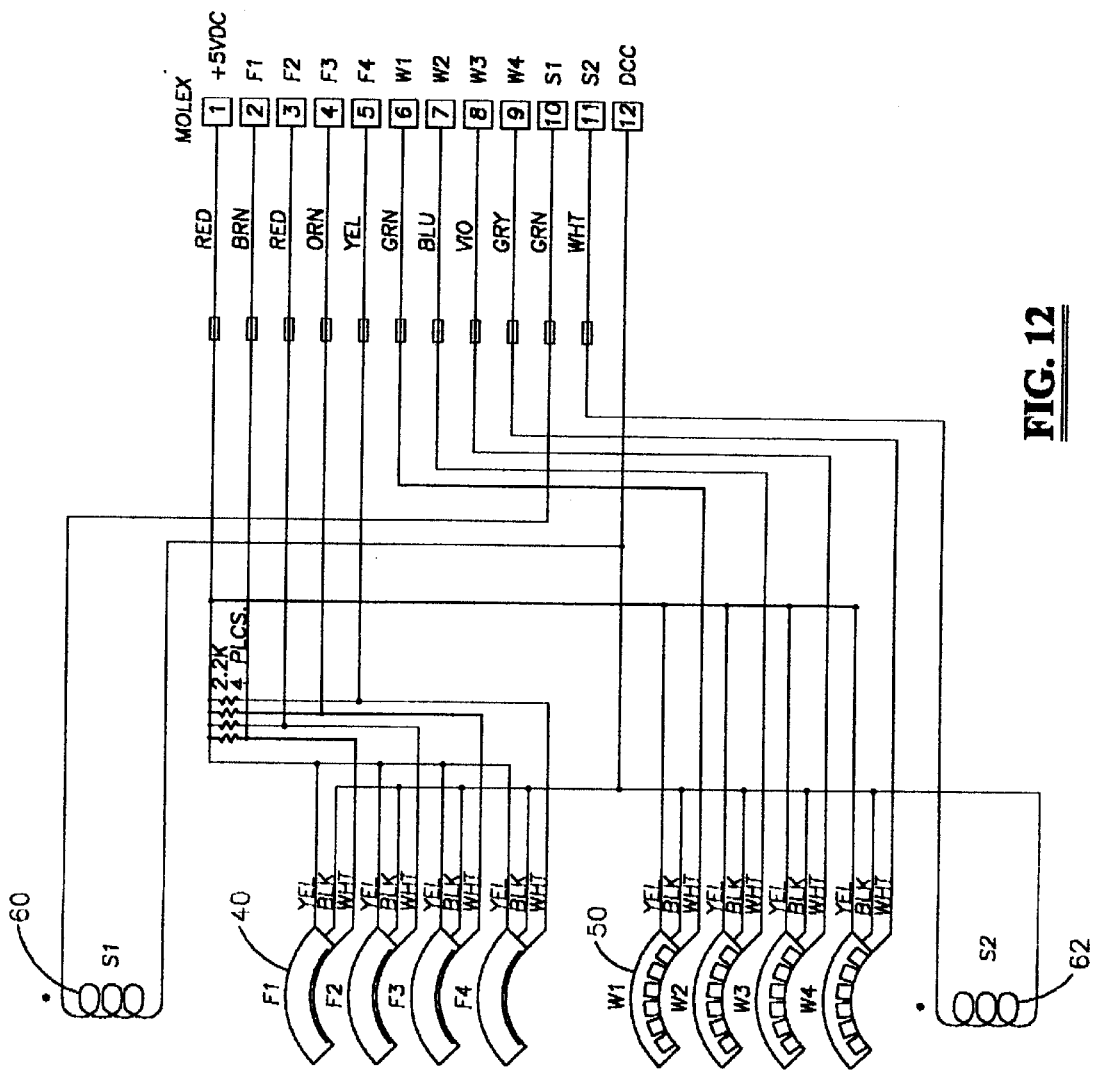

FIG. 12 illustrates in further detail the wiring for the inspection cartridge. Hall effect sensors or transducers monitor transverse flaws and wall thickness, as disclosed above, and the eddy current coils 60, 62 monitor for longitudinal splits. The Hall effect transducers 40 measure magnetic flux leakage and convert this leakage to a DC voltage output. The eddy current coils 60, 62 may be spaced in the desired selected distance apart, and the six inch spacing of these coils described earlier is exemplary.

Figure 13:
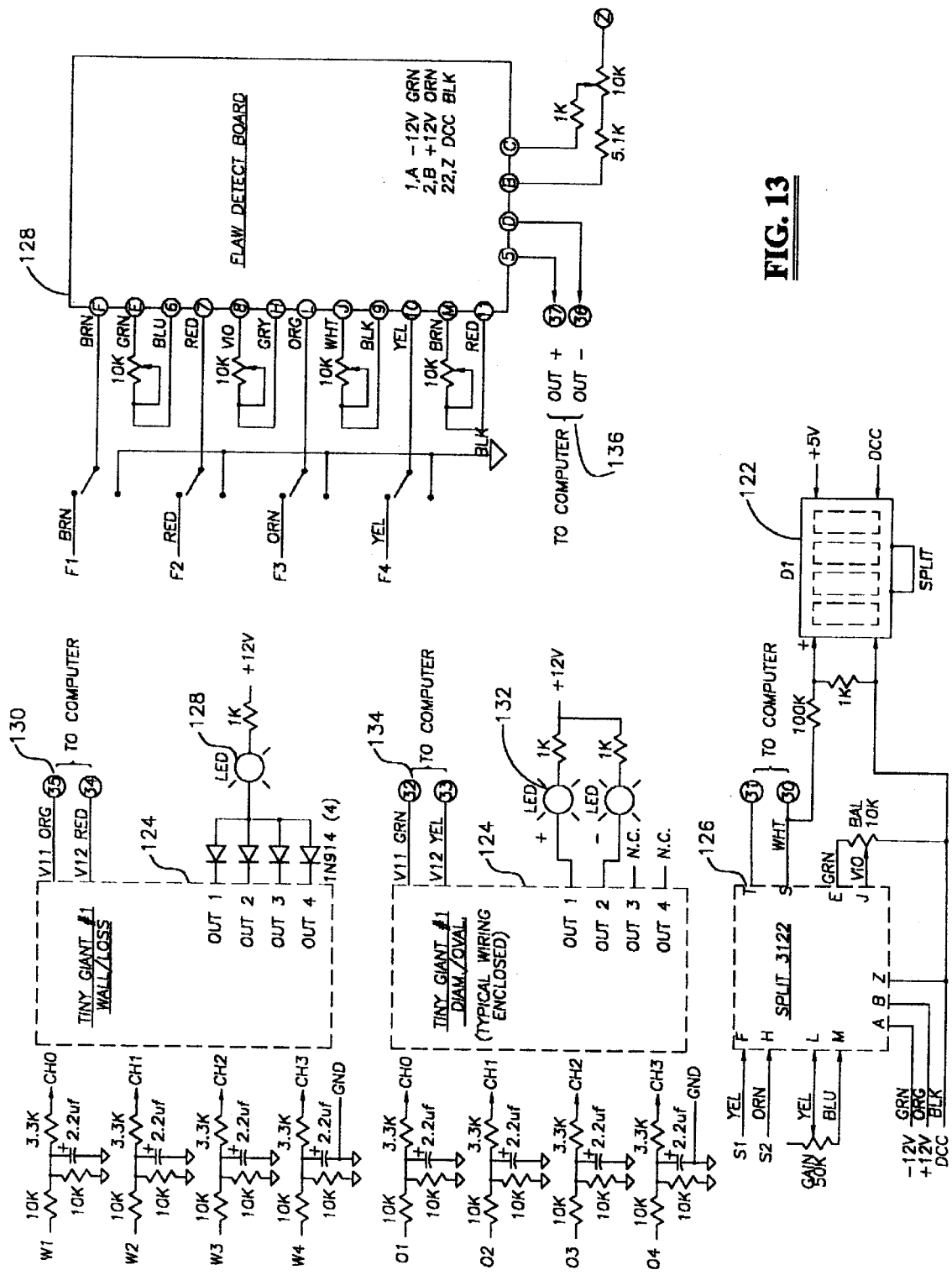
FIG. 13 is a circuit illustrating the wiring from a flaw detection board.

FIG. 13 depicts the panel wiring within the case 90. Primary components within the case 90 include one or more computers 124, an ITS 3122 split detector board 126 and a flaw detect board 128. The computer is used to detect wall thickness in the tubing while it is being inspected, i.e., in real time. The output voltage of the wall thickness transducers travels through the preamp wall section and then to the computer where the voltage is converted into a tubing wall thickness signal. The visual alarm 128 and output 130 to a main data storage computer are also provided. The computer uses the output voltage of the proximity switches to compute the diameter and ovality of the tubing. Another visual alarm 132 and output to the main data storage computer are also provided for these sensors. The ITS 3122 split detector board 126 operates as described above.

The flaw detect board 128 takes the output voltage of the flaw section of the preamp board and filters out unwanted noise, while providing an output 136 for the main computer. The flaw detect card ITS 3114 is a four channel flaw amplifier used to convert the transverse flaws to a voltage that is displayed on the main computer. The output of the flaw channels after pre-amplifications is sent through the signal cable to a single pole double throw switch. The signal then goes through a low frequency pass filter to help eliminate noise, then to the first gain stage amplifier. The gain level of this stage is set by adjusting the gain knob for that channel. From here, the signal is split into negative and positive components. Both of these signals pass through two more gain stages, then are recombined. At this point, a sample of the signal level is sent to a sensing circuit that turns on a light when the signal reaches a level set by the threshold knob. From this point, the four channels are combined and the signal is sent to a reject circuit that elimnates any indication that is below the reject knob setting. The signal is then split into negative and positive signals and sent to the main computer.

Another generation of the inspection system disclosed herein has explosion proof characteristics. Special explosion proof electrical components may thus be used. An array of permanent high energy, rare earth magnets, such as neodymium 27, serve as the magnetic generator. Electrical power thus need not be supplied to the magnetizing coil, since the permanent magnets would replace the magnetizing coil described herein.

The system of the present invention allows for the generation of tubing wall thickness output signals which may be automatically displayed to the operator as a percentage of the nominal tubing wall thickness. Similarly, the tubing diameter may be expressed as a percent of nominal diameter.

The computer record is a composite representation of the tubing characteristics. The inspector determines at the time of inspection whether to remove the flaw or just note on the computer record the fact that such flaw is present. Subsequent inspection will allow the inspector to further evaluate if any increase in flaw size occurs. The system may automatically generate and deposit on the tubing a paint marking or other indication of a defect to assist in locating tubing anomalies, which may subsequently be manually inspected with further equipment. A record of sensed tubing characteristics may be sent to a storage computer for future retrieval, and the data compared with other inspection runs.

The foregoing disclosure and description of the invention is illustrative and explanatory thereof, and it will be appreciated by those skilled in the art, that various changes in the size, shape and materials as well as in the details of the illustrated construction or combinations of features of the various ultrasonic test elements may be made without departing from the spirit of the invention.

What is claimed is:

1. A non-destructive inspection apparatus for testing tubulars, comprising:

a support housing;

an inspection head removably positioned within the support housing, the inspection head including a thru-bore for receiving a tubular passing axially through the inspection head;

a magnetic generator on the support housing for saturating the tubing while passing axially through the inspection head;

a plurality of flaw detector transducers on the inspection head circumferentially spaced about the thru-bore, each flaw detector transducer outputting a flaw detector electrical signal indicative of a change in flux leakage corresponding to a flaw in the tubular adjacent the respective flaw detector transducer;

a plurality of wall thickness transducers on the inspection head circumferentially spaced about the thru-bore, each wall loss transducer outputting a wall thickness electrical signal indicative of a change in density of magnetic flux corresponding to the wall thickness of the tubular adjacent the wall thickness transducer;

at least two pairs of diameter transducers on the inspection head, each of the at least two pairs of diameter transducers including a first diameter transducer and a second diameter transducer on a radially opposing sides of the thru-bore, a line extending between a first pair of diameter transducers defining a first axis, a line extending between a second pair of diameter transducers defining a second axis, the first axis being substantially inclined relative to the second axis, each first and second diameter transducer outputting an electrical signal indicative of the radial spacing between the respective transducer and an adjacent outer wall of the tubular;

a computer for processing electrical signals from the inspection head; and one or more electrical conductors for transmitting power to the inspection head and for transmitting electrical signals from the electrical head to the computer.

2. The non-destructive inspecting apparatus as defined in claim 1, further comprising:

each of the plurality of flaw detector transducers is positioned in one of a plurality of flaw detector arrays, each flaw detector array corresponding to a selected circumferential portion of the tubular; and the computer considers a maximum signal from the plurality of transducers in each array indicative of the largest flaw for determining characteristics of a defect in the tubular.

3. The non-destructive inspecting apparatus as defined in claim 1, further comprising:

each of the plurality of flaw detectors transducers has a substantially planar lower transducer surface aligned within a plane substantially parallel to and radially spaced from an adjacent outer surface of the tubular.

4. The non-destructive inspection apparatus as defined in claim 3, wherein:

each of the plurality of wall thickness transducers lies within a plane substantially perpendicular to each of the plurality of flaw detector transducers.

5. The non-destructive inspection apparatus as defined in claim 4, wherein the computer receives input from both the plurality of flaw detector transducers and the plurality of wall thickness detector transducers to determine if a sensed flaw should result in a rejection.

6. The non-destructive inspection apparatus as defined in claim 1, further comprising:

each of the plurality of wall thickness transducers is arranged in one of a plurality of arrays corresponding to a selected circumferential portion of the tubular; and the computer adds a wall thickness signal from each of the plurality of transducers in a respective array for determining wall thickness of the tubular adjacent the respective array.

7. The non-destructive inspection apparatus as defined in claim 1, wherein the computer adds the signal from the first diameter transducer and the signal from the second diameter transducer to determine an effective diameter of the tubular between the first and second transducers.

8. The non-destructive inspection apparatus as defined in claim 1, wherein the first axis is substantially perpendicular to the second axis.

9. The non-destructive inspection apparatus as defined in claim 1, wherein the computer compares the diameter of the tubular along the first axis to the diameter of the tubular along the second axis to determine the ovality of the tubular.

10. The non-destructive inspection apparatus as defined in claim 1, further comprising:

first and second axially spaced coils each positioned on the support housing and circumferentially surrounding the thru-bore;

an oscillator for providing high frequency power to each of the first and second coils;

a comparator circuit for comparing impedance in each of the respective first and second coils and outputting a signal indicative of a difference in impedance; and the computer compares the output signal to a preselected value to detect a longitudinal split in the coiled tubing.

11. The non-destructive inspection apparatus as defined in claim 10, wherein the oscillator has an adjustable frequency in excess of 500 Hz.

12. The non-destructive inspection apparatus as defined in claim 1, further comprising:

a plurality of centralizers each mounted to a support head for guiding the tubular passing axially through the inspection head.

13. The non-destructive inspection apparatus as defined in claim 12, further comprising:

a plurality of centralizers each mounted to a support head for guiding the tubulizer passing axially through the inspection head;

each centralizer including a rotational block for engagement with the tubular and a biasing member for biasing the rotational block toward engagement with the tubular; and an adjustment mechanism for radially adjusting the position of the rotational block with respect to the support housing.

14. The non-destructive testing apparatus as defined in claim 1, further comprising:

upstream and downstream end plates, at least one of the end plates being removably mounted to the housing for removably positioning the inspection head within the housing.

15. The non-destructive inspection apparatus as defined in claim 1, further comprising:

the magnetic generator is a magnetic coil; and the one or more electrical conductors supply electrical power to the magnetic coil.

16. The non-destructive inspection apparatus as defined in claim 1, further comprising:

a visual display panel for displaying an output from the computer to an operator.

17. A non-destructive inspection apparatus for testing tubulars, comprising:

a support housing;

an inspection head removably positioned within the support housing, the inspection head including a thru-bore for receiving a tubular passing axially through the inspection head;

a magnetic generator on the support housing for saturating the tubing while passing axially through the inspection head;

a plurality of flaw detector transducers on the inspection head circumferentially spaced about the thru-bore, each of the plurality of flaw detectors transducers has a substantially planar lower transducer surface aligned within a plane substantially parallel to and radially spaced from an adjacent outer surface of the tubular, each flaw detector transducer outputting a flaw detector electrical signal indicative of a change in flux leakage corresponding to a flaw in the tubular adjacent the respective flaw detector transducer;

a plurality of wall thickness transducers on the inspection head circumferentially spaced about the thru-bore, each of the plurality wall thickness transducers lies within a plane substantially perpendicular to an adjacent outer wall of the tubular, each wall loss transducer outputting a wall thickness electrical signal indicative of a change in density of magnetic flux corresponding to the wall thickness of the tubular adjacent the wall thickness transducer;

at least two diameter transducers each on the inspection head, the first diameter transducer being circumferentially spaced relative to the second diameter transducer, each diameter transducer outputting an electrical signal indicative of a diameter of the tubular along an axis passing through the respective diameter transducer;

first and second axially spaced coils each positioned on the inspection head each for providing an impedance signal to detect a longitudinal split in the coiled tubing; and a computer for processing electrical signals from the inspection head.

18. The non-destructive testing apparatus as defined in claim 17, further comprising:

upstream and downstream end plates, at least one of the end plates being removably mounted to the housing for removably positioning the inspection head within the housing.

19. A non-destructive inspection apparatus for testing tubulars, comprising:

a support housing;

an inspection head removably positioned within the support housing, the inspection head including a thru-bore for receiving a tubular passing axially through the inspection head;

at least two pairs of diameter transducers on the inspection head, each of the at least two pairs of diameter transducers including a first diameter transducer and a second diameter transducer on a radially opposing sides of the thru-bore, a line extending between a first pair of diameter transducers defining a first axis, a line extending between a second pair of diameter transducers defining a second axis substantially perpendicular to the first axis, each first and second diameter transducer outputting an electrical signal indicative of the radial spacing between the respective transducer and an adjacent outer wall of the tubular; and a computer for comparing the diameter of the tubular along the first axis to the diameter of the tubular along the second axis to determine diameter variations in the tubular indicative of necking, swelling and ovality of the tubular.

20. The non-destructive tubing apparatus as defined in claim 19, further comprising:

a magnetic generator on the support housing for saturating the tubing while passing axially through the inspection head;

a plurality of flaw detector transducers on the inspection head circumferentially spaced about the thru-bore, each of the plurality of flaw detectors transducers has a substantially planar lower transducer surface aligned within a plane substantially parallel to and radially spaced from an adjacent outer surface of the tubular, each flaw detector transducer outputting a flaw detector electrical signal indicative of a change in flux leakage corresponding to a flaw in the tubular adjacent the respective flaw detector transducer; and a plurality of wall thickness transducers on the inspection head circumferentially spaced about the thru-bore, each of the plurality wall thickness transducers lies within a plane substantially perpendicular to an adjacent outer wall of the tubular, each wall loss transducer outputting a wall thickness electrical signal indicative of a change in density of magnetic flux corresponding to the wall thickness of the tubular adjacent the wall thickness transducer.

* * * * *